United States Patent [19]
Hirohara et al.

[11] 4,146,432
[45] Mar. 27, 1979

[54] IMMOBILIZED PROTEASES

[75] Inventors: Hideo Hirohara; Shigeyasu Nabeshima, both of Ibaraki; Tsuneyuki Nagase, Takatsuki, all of Japan

[73] Assignee: Sumitomo Chemical Company, Limited, Osaka, Japan

[21] Appl. No.: 801,246

[22] Filed: May 27, 1977

[30] Foreign Application Priority Data

May 31, 1976 [JP] Japan .................................. 51-63890
Jun. 24, 1976 [JP] Japan .................................. 51-75118

[51] Int. Cl.² .............................................. C07G 7/02
[52] U.S. Cl. .................................. 195/63; 195/66 R; 195/68; 195/DIG. 11
[58] Field of Search .......... 195/63, 68, 66 R, DIG. 11

[56] References Cited

U.S. PATENT DOCUMENTS

| 3,597,220 | 8/1971 | Weinrich et al. .................. 195/63 X |
| 3,616,229 | 10/1971 | Wildi et al. ............................ 195/63 |
| 3,875,006 | 4/1975 | Belloc et al. ............................ 195/63 |

OTHER PUBLICATIONS

Matz et al., Isolation of Proteolytic Enzymes from Solution as Dry Stable Derivatives of Cellulosic Ion Exchangers, American Chemical Society Journal, vol. 81, 1959, pp. 4024–4028.
Zaborsky, O., Immobilized Enzymes, CRC Press, Cleveland, Ohio, 1973, pp. 75–82.

Primary Examiner—David M. Naff
Attorney, Agent, or Firm—Cushman, Darby & Cushman

[57] ABSTRACT

Non-specific proteases produced by bacteria belonging to the genus Streptomyces are immobilized by adsorption on a specific class of anion exchangers to produce water-insoluble enzymatically active immobilized proteases.

11 Claims, No Drawings

IMMOBILIZED PROTEASES

This invention relates to immobilization of proteases produced by bacteria belonging to genus Streptomyces. More particularly, this invention relates to a water-insoluble, enzymatically active immobilized protease composition which comprises non-specific proteases having esterase activities and amidase activities produced by bacteria belonging to the genus Streptomyces immobilized on an anion exchange polysaccharide having a total anion-exchange capacity of not less than 0.5 meq/g or a water-insoluble macroporous, highporous or macroreticulated anion-exchange resin having specific surface area of not less than 1 $m^2/g$ and a total anion-exchange capacity of not less than 0.5 meq/g, and also to a process for producing the same.

Enzymes are generally known to have substrate specificity, namely to have catalytic effect on specific substrates which are different depending on respective enzymes. However, bacteria belonging to the genus Streptomyces, e.g. *Streptomyces griseus, Streptomyces fradiae, Streptomyces erythreus, Streptomyces rimosus* and *Streptomyces flavovirens* are known to have a broad substrate specificity, namely to produce so called non-specific proteases. Such a broad specificity is due to the fact that bacteria belonging to the genus Streptomyces produce simultaneously several kinds of endoproteases and several kinds of exoproteases which are relatively similar in physical and chemical properties to one another. For example, proteases obtained from *Streptomyces griseus, Streptomyces fradiae* and *Streptomyces and erythreus* contain both endoproteases having substrate specificity such as the type of trypsin like activity, the type of chymotrypsin like activity, and the type of elastase like activity and exoproteases having substrate specificity such as the type of carboxypeptidase like activity and the type of aminopeptidase like activity. The type of trypsin like activity herein refers to protease having specificity on cationic amino acid residue such as of lysine or arginine; the type of chymotrypsin like activity to protease having specificity on large hydrophobic amino acid residue such as of tryptophan, tyrosine or phenyl alanine; and the type of elastase like activity to protease having specificity on small amino acid residue such as of glycine or alanine.

Thus, the non-specific proteases proteases produced by bacteria belonging to the genus Streptomyces can act on various substrates and therefore they are of a great practical value. Furthermore, these proteases have potent esterase and amidase activities not only on esters or amides of amino acids but also esters or amides of carboxylic acids in general. To be more specific, their catalytic effect is characterized by advantageous selective reactivity of an enzyme such that they act preferentially on L-isomer with little or no reaction with D-isomer. Therefore, the non-specific proteases produced by bacteria belonging to the genus Streptomyces are expected to be effective for optical resolution of esters or amides of amino acids or carboxylic acids having asymmetric carbons or introduction or chirality into prochiral molecules. Furthermore, proteases obtained from Streptomyces Sp. have many practical advantages such that they can be produced more cheaply and easily in a greater amount than proteases produced by animals.

On the other hand, an enzyme reaction is conducted by dissolving an enzyme in water thereby to allow the enzyme to act on a substrate in an aqueous solution. However, the fact that the enzyme reaction is a homogeneous reaction in an aqueous solution is a great hindrance to performance of continuous reaction in industrial applications and also makes it very difficult to recover remaining active enzymes for repeated use after the reaction. In addition, complicated operational procedures are necessary for separation and purification of the reaction product which is present in admixture with enzymes. From these standpoints, it is practically very valuable to immobilize the non-specific proteases thereby to make them water-insoluble.

There have hitherto been known various methods for immobilization of enzymes (refer to, for example, O. R. Zaborsky, "Immobilized Enzymes", C.R.C. Press, 1973 or "Immobilized Enzymes", edited by Ichiro Chihata, Kodansha, 1975). They can roughly be classified into the following four groups: (1) Physical or ionic adsorption method; (2) Covalent attachment method; (3) Entrapment method; and (4) Crosslinking method. Each of these methods has both advantages and disadvantages and it is difficult to decide which one is the best. From practical standpoint, however, the method with easier immobilization procedure is more advantageous. Adsorption method is the most advantageous in this respect.

In 1959, Mitz and Schleuter disclosed that trypsin and chymotrypsin were adsorbed on carboxymethyl cellulose, cellulose citrate and cellulose phosphate but the amount of the proteins adsorbed were very small and their activities were extremely deteriorated (Journal of the American Chemical Society, Vol. 81, p. 4024, 1959). Afterwards, there were made several attempts to immobilize these proteolytic enzymes on silica-alumina or gel-type ion exchange resins, whereby the adsorbed amount was very low and activity of immobilized enzyme was very low. As an attempt to immobilize crude proteases on carriers by adsorption, proteases obtained from bovine kidney and spleen have been adsorbed on diethylaminoethyl cellulose. However, the resultant crude proteases were extremely low in activity.

As a result of studies made about immobilization of proteases produced by bacteria belonging to the genus Streptomyces, it has now been found that a crude enzyme solution, which is low in specific activity and obtained just after removal by filtration of cells from a culture broth or after being merely subjected to preliminary purification procedure such as organic solvent precipitation method, can be mixed with an anion exchange polysaccharide having a total anion-exchange capacity of not less than 0.5 meq/g or a macroporous, highporous or macroreticulated anion-exchange resin having a total anion exchange capacity of not less than 0.5 meq/g and a specific surface area of not less than 1 $m^2/g$ to be readily immobilized thereon by adsorption; that the crude enzyme is partially purified through the immobilization procedure; that the immobilized enzyme is surprisingly increased by two to several times or more in esterase activities of the types of trypsin like activity, chymotrypsin like activity and elastase like activity and in aminopeptidase activity; and that, in some cases, an activity which is not detectable at all in crude enzymes may appear through the immobilization procedure.

The increase in activity effected through the immobilization procedure as mentioned above is not totally known in proteases of animal origin such as proteases from bovine kidney and spleen as mentioned previously. Thus, this procedure is practically of a great value as purification immobilization method of crude enzymes.

Even when crude enzymes are purified by salt-out, gel-chromatography or ion-exchange chromatography, the proteases produced by bacteria belonging to the genus Streptomyces possess the properties as mixed proteases. These partially purified or highly purified proteases are not enhanced in activity through the immobilization procedure. However, it has also been found that when an anion exchange resin having a total anion-exchange capacity of not less than 0.5 meq/g and a specific surface area of not less than 1 m$^2$/g is used as a carrier of adsorption immobilization of purified proteases, the proteases are immobilized by adsorption especially in a great amount; and further that the immobilized insoluble enzymes are stable with little leave-off, when attention is paid on the ionic strength of the reaction mixture to some extent, to prove that the present method is also particularly advantageous as immobilization method of the purified proteases produced by bacteria belonging to the genus Streptomyces.

An object of the present invention is to provide a water-insoluble, enzymatically active enzyme composition which is obtained by adsorbing non-specific proteases having esterase activities and amidase activities produced by bacteria belonging to the genus Streptomyces on an anion-exchange polysaccharide having a total anion-exchange capacity of not less than 0.5 meq/g or a macroporous, high-porous or macroreticulated anion-exchange resin having a specific surface area of not less than 1 m$^2$/g and a total anion-exchange capacity of not less than 0.5 meq/g.

The other object of the present invention is to provide a method for immobilizing the aforesaid crude proteases simultaneously with purification thereof by treating said proteases with the anion-exchanger or anion-exchange resins as described above.

The anion-exchange polysaccharide to be used in the present invention may include anion-exchange celluloses such as diethylaminoethyl cellulose (DEAE-cellulose), triethylaminoethyl cellulose (TEAE-cellulose), guanidoethyl cellulose (GE-cellulose) and the like; and anion-exchange Sephadex such as diethylaminoethyl Sephadex (DEAE-Sephadex), diethyl-2-hydroxylpropylaminoethyl Sephadex (QAE-Sephadex) and the like. Among them, DEAE-Sephadex and QAE-Sephadex are particularly preferred. "Sephadex" refers herein to trade names of cross-linked dextran (Pharmacia Fine Chemical Co.).

As an anion-exchange resin having a specific surface area of not less than 1 m$^2$/g and a total anion-exchange capacity of not less than 0.5 meq/g which is an immobilization carrier of the present invention, there may be used, among ion-exchange resins or adsorbent resins known under the trade marks such as Amberlite, Dowex, Duorite and Diaion, those which have anion-exchange groups and are commercially available macroporous, highporous or macroreticulated anion-exchange resins with large specific surface area and porosity which are often called as MR (macroreticular) type, MP (macroporous) type, macronetwork structure type or highporous type. The anion-exchange resins may alternatively be prepared by various conventional methods. For example, a macroporous resin can be obtained by permitting a compound inert to polymerization to be present in a polymerization system when styrene is copolymerized with suitable amount of divinyl benzene to prepare an ion-exchange resin matrix and after the polymerization, removing said compound by extraction with a solvent from the resulting resins obtained. This resin matrix is then subjected to chloromethylation of the resin matrix, followed by amination by conventional method, whereby a macroporous resin having anion-exchange groups can be obtained.

The water-insoluble enzymatically active composition of the present invention can be prepared by first treating ion-exchangers by conventional method with an aqueous hydrochloric acid solution (0.01 to 3 M conc., preferably 0.05 to 1 M conc.) or an aqueous caustic soda solution (0.01 to 3 M conc., preferably 0.05 to 1 M) to activate ion-exchange groups or making the resins buffered at pH 5.5 to pH 8.5 with a suitable buffer solution (0.01 to 3 M conc., preferably 0.05 to 1 M) having buffer action within the range between pH 5.5 and pH 8.5 such as a phosphate buffer solution or a borate buffer solution, then immersing the thus treated anion-exchanger in a buffered enzyme solution for sufficient time, followed by stirring, if desired, and thereafter recovering the anion-exchanger, followed by filtration and washing. The immobilization by adsorption is carried out at a temperature of 40° C. or lower, more preferably around 4° C. The adsorption time is desirably two hours or longer. The thus obtained water-insoluble proteases have high esterase, amidase and peptidase activities and are stable, provided that they are not washed with saltous solutions having high ionic strength. If desired, they may be dried by such a method as lyophilization so as to be storable for a long time and convenient for transportation.

The said enzymes can be adsorbed in an amount of 400 mg per one gram of the anion-exchanger at its maximum, depending on the kinds, the specific surface area and porosity of the anion-exchanger employed.

The following examples are given for the purpose of illustration only and it is not intended to limit the present invention thereto.

EXAMPLE 1

1.0 Gram of DEAE-Sephadex A-25 (ion-exchange capacity: 3.5 meq/g) was treated with 0.1 N caustic soda for activation and then washed well with water repeatedly. On the other hand, 40 mg of crude protease produced by bacteria belonging to the genus Streptomyces (with activity of 12.0 $\mu$moles/mg.hr on N-benzoyl-L-algine ethyl ester (BAEE) under turn-over conditions at pH 8.0 and 30° C.) was dissolved in 20 ml of tris-hydrochloric acid buffer solution (pH 8.0, I=0.1). Into this solution was immersed 1.0 g of the previously activated DEAE-Sephadex A-25 and stirring was continued slowly at 4° C. for 6 hours. After suction filtration with a glass filter, the anion-exchanger absorbing the enzyme was washed well with pure water and a tris-hydrochloric buffer solution with pH 8.0 and ionic strength of 0.1. The amount of enzymes adsorbed was determined from the absorption strength of ultra-violet absorption spectrum of the filtrate recovered to be 36 mg. The percentage of immobilization was found to be 90%, and the activity of the immmobilized enzyme on BAEE was, when measured under the same conditions used for measurement of activity before immobilization, found to be 63 $\mu$moles/mg.hr. The activity of this immobilized enzyme was measured by batch method with pH-stat at pH 8.0 and 30° C. once per day. After 14 days, it maintained an activity of as high as 60 $\mu$moles/mg.hr.

EXAMPLE 2

Example 1 was repeated, except that Amberlite IRA-93 (ion-exchange capacity: 4.6 meq/g) was used in place of the DEAE-Sephadex and the pH at the time of immobilization and measurement was changed from 8.0 to 7.2, to carry out similar immobilization procedure and activity measurement. The amount of immobilized enzyme was found to be 34 mg and the enzyme activity in a solution before immobilization, which was 6.5 $\mu$moles/mg.hr to BAEE at pH 7.2, was elevated by immobilization to 32 $\mu$moles/mg.hr.

EXAMPLE 3

To 2.0 g of DEAE-Sephadex A-25 activated with 0.1 N NaOH was added 200 mg of a crude protease produced by *Streptomyces fradiae* (activity on BAEE: 6.3 $\mu$moles/mg.hr, at pH 7.2 and 30° C.) and the mixture was stirred slowly at 4° C. overnight to accomplish adsorption. The adsorbed amount was measured by ultra-violet absorption strength of the recovered liquid to be 128 mg. The activity for BAEE was enhanced by immobilization to 36 $\mu$moles/mg.hr, the percentage of activity increase being 570%. The activity on the amide type specific substrate N-benzoyl-DL-argenine-p-nitroanilide was also increased by immobilization by 610%.

Five ml of this immobilized protease was packed in a column of 7 mm$\phi$ × 150 mm equipped with a jacekt and a 0.05 M BAEE solution adjusted at pH 7.0 was passed through the column from the upper end thereof at the rate of SV=2.0, while maintaining the column temperature at 30° C. From quantitative analysis by hydroxylamine method of the amount of unaltered esters in the effluent, 98% was found to be hydrolyzed. This reaction was continued for 12 days, one hour per day, by continuous column passage method, whereby the activity was lowered only by 11%.

EXAMPLE 4

To 1.0 g of QAE-Sephadex (ion-exchange capacity: 3.0 meq/g) buffered with 0.2 M phosphate buffer solution (pH 7.2) was added 80 mg of a crude non-specific protease produced by bacteria belonging to the genus Streptomyces and the mixture was stirred slowly at 4° C. for 6 hours to accomplish adsorption. The amount of the enzyme adsorbed was calculated by ultra-violet absorption strength of the liquid recovered by washing to be 70 mg. For evaluation of the type of chymotrypsin like activity, activity on N-acetyl-L-tryptophan ethyl ester (ATEE), which was a specific substrate for $\alpha$-chymotrypsin, was measured. The activity on ATEE at pH 7.2 and 30° C. was found to be 7.3 $\mu$moles/mg.hr for enzyme solution before immobilization and 19 $\mu$moles/mg.hr for immobilized enzyme. The activity on 7th day after immobilization was 18 $\mu$moles/mg.hr.

EXAMPLE 5

Immobilization and activity measurement were conducted under the same conditions as in Example 4 except that the immobilization carrier was changed from QAE-Sephadex to Duorite A 161 (ion-exchange capacity: 3.5 meq/g). The amount of immobilized enzyme was 64 mg and the activity of the immobilized enzyme 16.5 $\mu$moles/mg.hr.

EXAMPLE 6

For evaluation of the elastase type activity of the crude enzyme used in Example 1, there was measured activity on N-benzoyl-DL-alanine methyl ester (BAlME) which is a specific substrate for elastase. Before the immobilization, no activity was observed at the reaction temperature 40° C. at pH of 7.1 and 8.0. Then, 52 mg of the crude enzyme was immobilized by adsorption on 1 g of DEAE-Sephadex A-25 in a phosphate buffer solution at pH 7.1 (immobilization percentage: 87%). The immobilized enzyme exhibited activity on BAlME of 36 $\mu$moles/mg.hr at pH 7.1 and 35° C., whereby only L-isomer was found to be reactive. This result shows that crude enzyme can be purified without immobilization of inhibitors through the adsorption immobilization procedure on DEAE-Sephadex A-25. When this immobilized enzyme was used for 6 days, one to several times per day, by batch method, the activity was found to be lowered only by 4.7%.

Subsequently, the immobilized enzyme was washed with 5 M aqueous NaCl solution and 0.5 M phosphate buffer solution to elute and recover the enzyme. Recovery was 86% of the immobilized enzyme. The activity of the recovered enzyme in the state of a solution on BAEE was measured at 30° C. and pH 8.0 to be 68 $\mu$moles/mg.hr and on BAlME at 35° C. and pH 7.1 to be 37 $\mu$moles/mg.hr.

EXAMPLE 7

1.0 Gram of a macroporous anion-exchange resin Duorite A-161 was treated with 1/50 N caustic soda, followed by thorough washing with water. This resin was added into an aqueous solution in which 100 mg of Pronase E, which is the commercially available group of purified proteases produced by *Streptomyces griseus*. After the mixture was stirred slowly at 5° C. for 5 hours to adsorb the enzyme on the resin, it was subjected to suction filtration with a glass filter and washed thoroughly with 0.05 M (pH 7.0) phosphate buffer solution and water. The filtrate and washings were recovered and, from the ultra-violet adsorption strength at 280 nm of the recovered solution, the amount of the enzyme immobilized by adsorption on the resin was calculated to be 86 mg. The specific activity of this immobilized enzyme was measured using BAEE as substrate with pH stat (Hiranuma precision pH stat PS-11) at pH 7.0 and 30° C. under the condition of excess substrate over enzyme to be 3.8 $\mu$moles/mg.min (specific activity of liquid enzyme under the same measurement conditions being 9.0 $\mu$moles/mg.min). Accordingly, the total activity of the immobilized enzyme was 326 $\mu$moles/min. This immobilized enzyme maintained 88% of the activity after 10 days after immobilization.

EXAMPLE 8

After 1.0 g of a macroporous anion-exchange resin Amberlite IRA-93 was buffered with 0.1 M phosphate buffer solution (pH 7.0), it was immersed in 20 ml of 0.05 M phosphate buffer solution having 100 mg of an enzyme dissolved therein. The enzyme used was produced by culturing *Streptomyces fradiae* (ATCC 15438) by conventional method in Basal medium for three days, subjecting the culture broth to filtration, salt-out with ammonium sulfate (60% saturated solution) and acetone precipitation, followed further by chromatography treatment with DEAE-cellulose and lyophilization. While stirring the mixture of the resin and the enzyme in the buffer solution slowly at 4° C. for 5 hours, the enzyme was immobilized by adsorption on the resin. The amount of the immobilized enzyme was calculated from the ultra-violet absorption strength of the protein in the recovered liquid to be 92 mg. The activity of the immobilized enzyme, when measured under the turnover conditions at 40° C. and pH 7.0 using BAEE as substrate, was 4.1 μmoles/mg.min which was 82% of that of the liquid state enzyme before immobilization. The immobilized enzyme was packed in a column of 7 mm in diameter and 140 mm in height equipped with a jacket and a 0.2 M BAEE solution adjusted at pH 7.0 was passed through the column from the upper end thereof at the rate of SV=12, while maintaining the column temperature at 40° C. The amount of unaltered esters in the effluent was analyzed quantitatively to find that 100% thereof was hydrolyzed. The residual activity of the immobilized enzyme column after continued use for 10 days was as much as 80%.

EXAMPLES 9-13

Immobilization was effected by the same procedure as in Example 7 by varying the resins as shown in the Table below. Measurements of activities were conducted under the same conditions as in Example 7 to give the results as listed in the same Table.

In Examples 10 and 12, there was used the enzyme obtained similarly as in Example 8; in other Examples, the same commercially available Pronase E as in Example 7 was used. The specific surface area of each resin was measured, after vacuum drying each resin with heating at 60° C., by BET method by means of gas adsorption type surface area measuring instrument. As reference example, the result obtained by immobilizing trypsin on a gel-type ion-exchange resin is also shown in the same Table.

| Example | Name of Ion Exchange Resin | Specific surface area (m²g) | Substrate* | Total activity (μmoles/min) | | Percentage of immobilization (%) |
|---|---|---|---|---|---|---|
| | | | | Liquid state enzyme | Immobilized enzyme | |
| 9 | Duorite S-37 | 95.3 | BAEE | 618 | 392 | 63.4 |
| 10 | Dowex MWA-1 | 5.6 | BAME | 53 | 49 | 92.4 |
| 11 | Amberlite IRA 900 | 26 | ATEE | 153 | 104 | 68.0 |
| 12 | Diaion SA 316 | 3 | BAEE | 195 | 121 | 62.1 |
| 13 | Duorite A-161 | 6.8 | BAME | 75 | 72 | 96.0 |
| Reference example (enzyme: trypsin) | Amberlite IR-1217 | 0.1> | BAEE | 189 | 3 | 1.6 |

*ATEE:N-acetyl-L-tyrosine ethyl ester
BAME:N-benzoyl-DL-alanine methyl ester

What we claim is:

1. A water-insoluble, enzymatically active immobilized protease composition which comprises enzymatically active proteases produced by bacteria belonging to the genus Streptomyces immobilized by adsorbing on a water-insoluble macroporous, macroreticulated anion-exchange resin having specific surface areas of not less than 1 m²/g and a total anion-exchange capacity of not less than 0.5 meq/g.

2. An immobilized protease composition according to claim 1, wherein proteases produced by bacteria belonging to the genus Streptomyces have esterase activities and amidase activities.

3. An immobilized protease composition according to claim 1, wherein proteases produced by bacteria belonging to the genus Streptomyces and non-specific proteases having chymotrypsin activity, trypsin activity and elastase activity.

4. An immobilized protease composition according to claim 1, wherein proteases produced by bacteria belonging to the genus Streptomyces having endoprotease activity and exoprotease activity.

5. An immobilized protease composition according to claim 1, wherein proteases produced by bacteria belonging to the genus Streptomyces are crude.

6. An immobilized protease composition according to claim 1, wherein proteases produced by bacteria belonging to the genus Streptomyces are partially purified or highly purified.

7. An immobilized protease composition according to claim 1 wherein the genus Streptomyces is selected from the group consisting of *Streptomyces griseus, Streptomyces fradiae, Streptomyces erythreus, Streptomyces rimosus* and *Streptomyces flavovirens.*

8. A process for producing a water-insoluble enzymatically active immobilized protease composition from proteases produced by bacteria belonging to the genus Streptomyces which comprises contacting the proteases with a water-insoluble macroporous, macroreticulated anion exchange resin having specific surface areas of not less than 1 m²/g and a total anion-exchange capacity of not less 0.05 meq/g to adsorb said proteases on said resin.

9. A process according to claim 8, wherein proteases produced by bacteria belonging to the genus Streptomyces are non-specific proteases having chymotrypsin activity, trypsin activity and elastase activity.

10. A process according to claim 8 wherein proteases produced by bacteria belonging to the genus Streptomyces have esterase activities and amidase activities.

11. A process according to claim 8, wherein the genus Streptomyces is selected from the group consisting of *Streptomyces griseus, Streptomyces fradiae, Streptomyces erythreus, Streptomyces rimosus* and *Streptomyces flavovirens.*

* * * * *